United States Patent [19]

Darnand

[11] Patent Number: 5,100,317
[45] Date of Patent: Mar. 31, 1992

[54] DEVICE AND METHOD FOR FABRICATING A PROSTHESIS

[76] Inventor: Jean J. Darnand, 13 rue Jean Mermoz, 71000 Macon, France

[21] Appl. No.: 582,968

[22] PCT Filed: Jan. 31, 1990

[86] PCT No.: PCT/FR90/00075
§ 371 Date: Oct. 1, 1990
§ 102(e) Date: Oct. 1, 1990

[87] PCT Pub. No.: WO90/08513
PCT Pub. Date: Aug. 9, 1990

[30] Foreign Application Priority Data
Jan. 31, 1989 [FR] France .................. 89 01452

[51] Int. Cl.$^5$ ........................... A61C 11/00
[52] U.S. Cl. ......................... 433/60; 433/54
[58] Field of Search ............ 433/53, 54, 57, 60, 433/213

[56] References Cited

U.S. PATENT DOCUMENTS

| | | | |
|---|---|---|---|
| 4,103,424 | 8/1978 | Benjamin et al. | 433/58 |
| 4,128,942 | 12/1978 | Schleich | 433/60 |
| 4,200,981 | 5/1980 | Fine | 433/60 |
| 4,323,346 | 4/1982 | Beu | 433/58 |
| 4,358,269 | 11/1982 | Hay et al. | 433/60 |
| 4,842,242 | 6/1989 | Huffman | 249/54 |

FOREIGN PATENT DOCUMENTS

| | | |
|---|---|---|
| 0151086 | 8/1985 | European Pat. Off. |
| 2139092 | 11/1984 | United Kingdom ........ 433/54 |
| 2169548 | 7/1986 | United Kingdom |

*Primary Examiner*—John J. Wilson
*Assistant Examiner*—Cindy A. Cherichetti
*Attorney, Agent, or Firm*—Parkhurst, Wendel & Rossi

[57] ABSTRACT

Device for making plaster models, total or partial dental arch replicas, used for dental reconstitutions and mounted on an occlusion device or articulator, comprising two articulated parts, respectively a higher part (1) and a lower part (2), and each having a reception cup (3). Each cup (3) receives a removable cupel of which the peripheral external wall (8) assumes the shape of the internal wall of the cup (3), said cupel (6) being set in the cup (3) when making the model; each cup (3) is comprised of removable fixing means (5, 11, 12) for fixing the cupel (6).

9 Claims, 4 Drawing Sheets

DEVICE AND METHOD FOR FABRICATING A PROSTHESIS

The invention relates to a device designed to be used when making dental prostheses from an impression taken in the mouth of the patient. It also relates to the method for using this device.

As is known, the production of a dental prosthesis involves first obtaining the exact replica of the dental arches to be reconstituted and/or restored. This replica, generally designated by the term "model" or "cast", is obtained by simple casting of a mold called an "impression". The impression is taken in the mouth of the patient directly by the dental surgeon, using a material of the alginate or silicone type.

Various types of impression-taking are carried out nowadays, namely, first of all, the so-called "total" impressions, which enable a complete model to be obtained for each of the two dental arches, then the so-called "partial" impressions, giving a partial model of one arch; finally, the partial impressions also called "bites", corresponding to a double partial impression, respectively the upper part and lower part simultaneously, both in the occlusion relation.

In a general manner the casting of the impressions is effected by simple filling, generally using plaster. The reproduction of the teeth and of the gingiva is first carried out. This reproduction is then placed on a plaster base with a view to producing a stable model. Once the upper and lower models corresponding to a given bite are cast for one and the same mouth, the dental prosthesist positions them in accordance with their occlusion relation, and this in as representative a manner as possible relative to the actual situation in the mouth. To do this, he uses an "occlusion device" or "articulator", that is to say an apparatus on which there are articulated two substantially parallel branches receiving the two upper and lower models.

European Patent EP-A0,151,086 describes, for example, a device permitting the preparation and the positioning of elements formed by reproducing the partial dentition of a patient and its gingival contour, extended by any positioning system called a "die" in the profession, in the field of dental prostheses. This device is employed using an occlusion device or articulator.

U.S. Pat. No. 4,496,320 also describes an occlusion device or articulator of the type in question, designed to permit the production of prostheses from impressions. This articulator consists of two plates fixed on the actual articulation device itself, the two plates each receiving one of the two impressions, upper or lower.

Similarly, British Patent GB-A-2,169,548 describes a device designed to permit the production of impressions, consisting of a serrated base. The impressions are cast directly on the serrated base. The prosthesist can then cut off the plaster and incorporate the various elements of the impression (dies) in accordance with the actual position in the mouth, without using pins.

All these devices present major disadvantages. First, their use necessitates a complex and generally expensive articulator. Moreover, and in particular, they do not take into account the natural expansion of the plaster during its solidification. It should be noted that even when a plaster of low expansion is used, which is moreover very expensive, the results obtained are not satisfactory. Indeed, the re-use of a solidified cast to represent again the impression in the articulator results in a different positioning from the initial positioning, on account precisely of the deformations observed by the expansion during the solidification of the plaster. In other words, deviations on the order of one to five tenths of a millimeter are commonly observed with this type of device, these being incompatible with the required quality and accuracy for the work of the prosthesist, and often being prejudicial as regards the resulting comfort of the patient. These deviations may in fact be at the origin of so-called overbite phenomena, that is to say that the bite of the artificial teeth does not correspond to that of the natural teeth.

SUMMARY OF THE INVENTION

The invention arms to overcome above discussed disadvantages. It concerns a device capable of facilitating the work of the prosthesist, while at the same time improving the quality of the prostheses obtained, and of reducing their cost price. It also concerns a method for using this device. These results are achieved by taking into account and controlling the natural expansion of the plaster.

The invention relates to a device permitting the production of plaster models, total or partial dental arch replicas, used for dental reconstitutions, and mounted on an occlusion device or articulator, comprising two articulated parts, respectively upper and lower, and each comprising a receiving cup.

The device is characterized:
in that each cup receives a removable cupel, of which the external peripheral wall matches the internal wall of the cup, said cupel being designed to be engaged in the cup when making the model;
and in that each cup comprises removable means for fixing said cupels.

In other words, the invention consists in providing the adapted branches of the occlusion devices or articulators of a type known per se with a cupel able to receive the plaster constituting the model, and in providing for a removable attachment of said cupels on the cup-shaped branches of the occlusion device and/or articulator. The cupels in which the plaster is cast in fact acts as a bridle on the expansion of said plaster.

The cup advantageously has an elongate and closed peripheral contour, having at its free end a longitudinal screw able to brace the cupel when the latter is in position.

The corresponding wall of the cupel, designed to come close to said longitudinal screw, has a cutting able to receive the end of said longitudinal clamping screw.

The clamping screw advantageously has a needle able to cooperate with the cutting in the cupel in the form of a conical recess, the latter being aligned with the axis of the needle, the latter being slightly offset relative to the generatrix of the cone of the cutting when the cupel is in position, in such a way that, after the plaster has been poured into said cupel, the latter is displaced slightly towards the base of the cup by the clamping action of the screw until the generatrix of the cone coincides with the axis of the needle.

In another embodiment the cupel has an open base permitting access to the surface of the model opposite that bearing the replica of the teeth. This arrangement is particularly advantageous in the context of the use of needles for supporting assemblies consisting of the plaster and the reconstitution, commonly designated "pins" in the technical field in question.

The cupel advantageously has a peripheral shoulder in order to limit its penetration into the cup.

The cupel also advantageously has at its end near its rear base an attachment lug projecting outwards.

The cupel is advantageously made of high-impact polystyrene and the cup of polyacetal.

In another embodiment, the walls of the cupel have transverse orifices designed to permit an improvement in the anchoring of the plaster at the time of its casting. At the same time, they can also have incipient break points designed to permit the release of the model after use.

The invention also relates to a method for using the device. This method is characterized in that it consists:
 in inserting and fixing the cupel in the cup;
 in filling the cupel with liquid plaster;
 in positioning and driving into this liquid plaster the first part (denture) of the model;

After hardening of the plaster, a complete model is therefore available whose lower part, fixed to the cupel, constitutes a removable base which can be retained as such and positioned again when desired in a cup associated with an articulator or occlusion device.

BRIEF DESCRIPTION OF THE DRAWINGS

The manner in which the invention can be achieved and the advantages which derive therefrom will emerge more clearly from the following illustrative embodiment, given by way of non-limiting example, with reference to the attached figures in which.

DETAILED DESCRIPTION OF THE INVENTION

Figure 7:
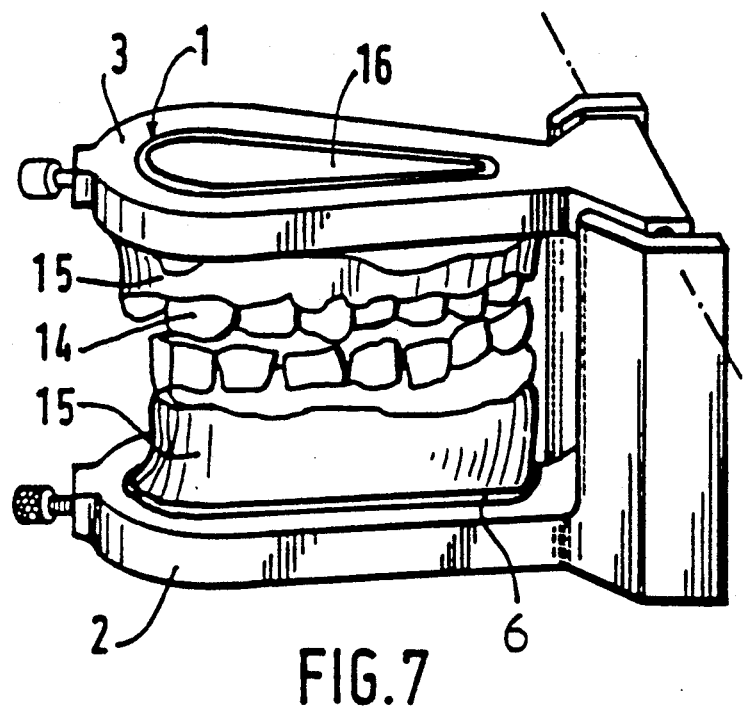
FIG. 7 illustrates the method of production on an articulator or occlusion device of two prosthesis models produced according to the invention.

As can be seen in FIG. 7, an occlusion device or articulator according to the invention basically consists of two branches (1) and (2) facing each other, in the shape of a cup (3). These two cups (3) are designed to each receive a model, respectively upper and lower corresponding to a given bite, and this in accordance with the occlusion relation corresponding to the actual occlusion relation in the mouth of the patient in question.

According to the invention, the cups (3) constituting the branches (1) and (2) are of overall elongate and even ovoid form, round if appropriate. They do not have any base. They are made of plastic material, for example polyacetal resin, and have on one of their lateral surfaces means (not shown) for attachment to the actual articulator or occlusion device itself. These means can consist of simple lateral lugs, designed to cooperate with complementary recesses in the occlusion device.

Referring to FIGS. 1-5, cup (3) has on one of its lateral surfaces, and on the side opposite the side designed to receive the model, a notch (4) produced by molding and designed to cooperate with a corresponding element on the cupel (6) as described later.

The lateral surface opposite the preceding surface has a threaded transverse orifice (5) situated in the main axis of said cup (3). This orifice is designed to receive a clamping screw (12) for the purpose of removably fixing the cupel (6) in the cup (3), as described hereinafter.

In accordance with the invention, this cup (3) is designed to receive a cupel (6) of a shape adapted to the internal walls of said cup (3). This cupel (6), made of plastic material, for example high-impact polystyrene, is thus also of elongate form. In the example described the cupel (6) has no base.

According to the invention, the cupel (6) has a peripheral shoulder (7) which extends outwards and is designed to limit the penetration of the cupel (6) into the cup (3).

According to an advantageous form of the invention, the peripheral wall (8) defining the cupel (6) presents a slight clearance, resulting in a widening in the direction of the outside and in particular in the direction of the peripheral shoulder (7). This peripheral wall (8) may advantageously comprise transverse orifices (21), designed to improve the anchoring of the plaster capable of filling the cupel (6).

The cupel (6) has, at one of its ends and on the surface opposite the surface presenting the shoulder (7), a lug (9) directed toward the outside, and designed to cooperate with the notch (4) formed in the cup (3). As will be described later, this lug (9)/notch (4) cooperation constitutes one of the points of attachment of the cupel (6) on the cup (3). The cupel (6) has, on the lateral surface opposite the surface comprising the lug, a cutting in the form of a conical recess (10), designed to cooperate with the point (11) of a screw (12) screwed into the threaded orifice (5) formed in the cup (3). The point (11) of the screw (12) is in fact advantageously a needle, whose axis is aligned with the principal axis of the cup and, thus, of the cupel (6), and slightly offset relative to the generatrix of the cone of the recess (10) when the cupel (6) is simply in position in the cup (3). In this way, by screwing the screw (12) into the orifice (5), the conical shape of the needle (11) cooperating with the conical recess (10) in the cupel causes, in addition to a bracing of the latter, its relative penetration into the cup (3).

Figure 1:
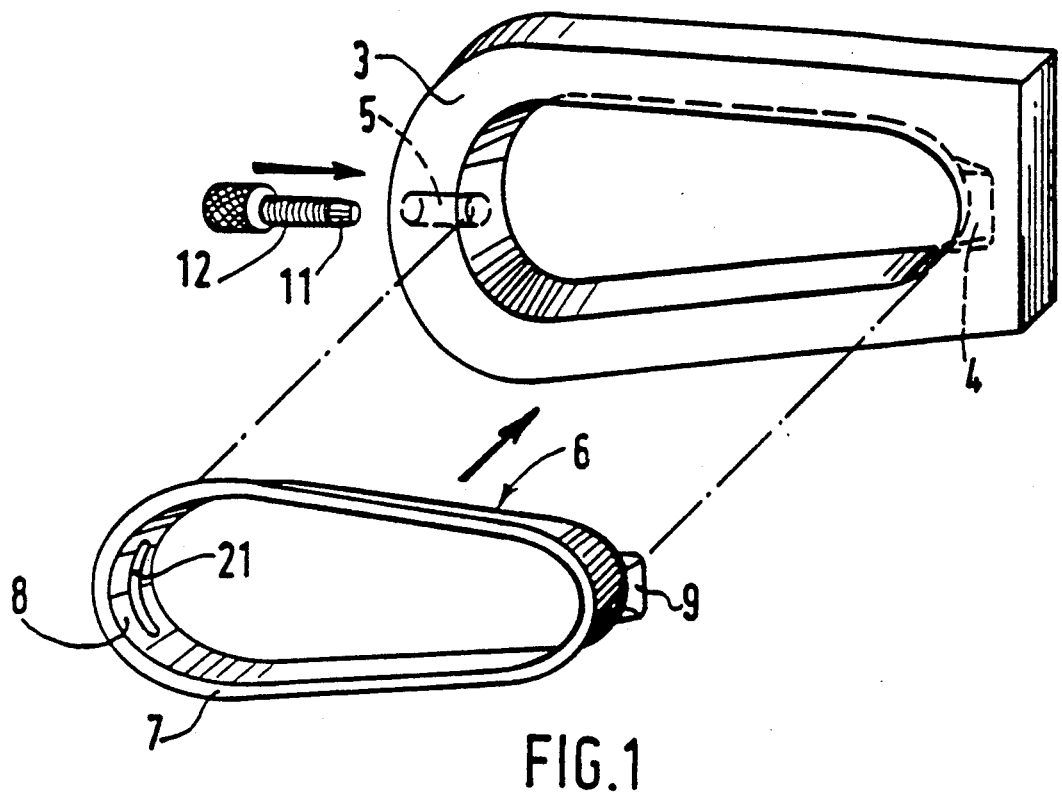
FIG. 1 is a perspective view of a device according to the invention before assembly.
Figure 2:
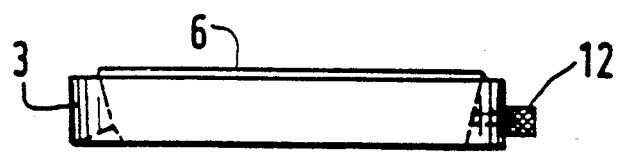
FIG. 2 is a side view of the cupel engaged in the cup.
Figure 3:
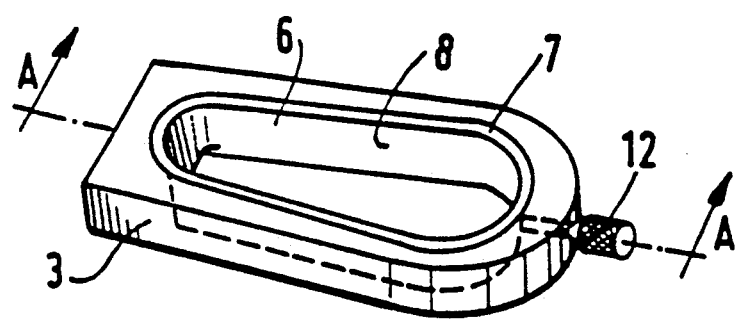
FIG. 3 is a perspective view.
Figure 4:
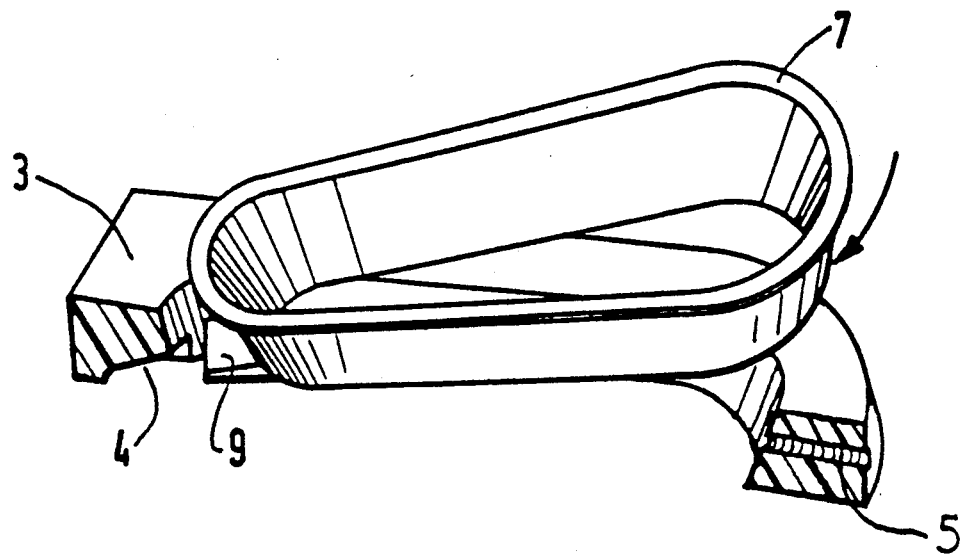
FIG. 4 shows the stage of presentation of the cupel on the cup.
Figure 5:
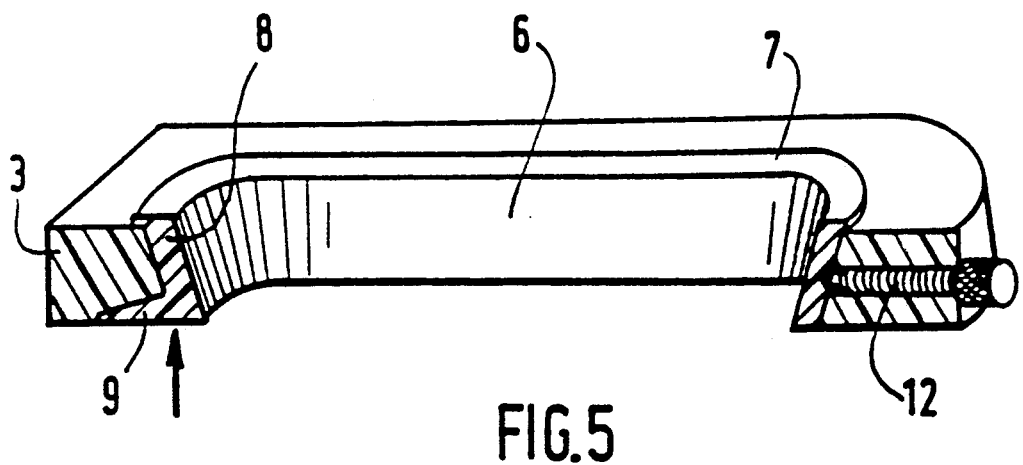
FIG. 5 is a section along the line A-A in FIG. 3 of the assembly.
Figure 6:
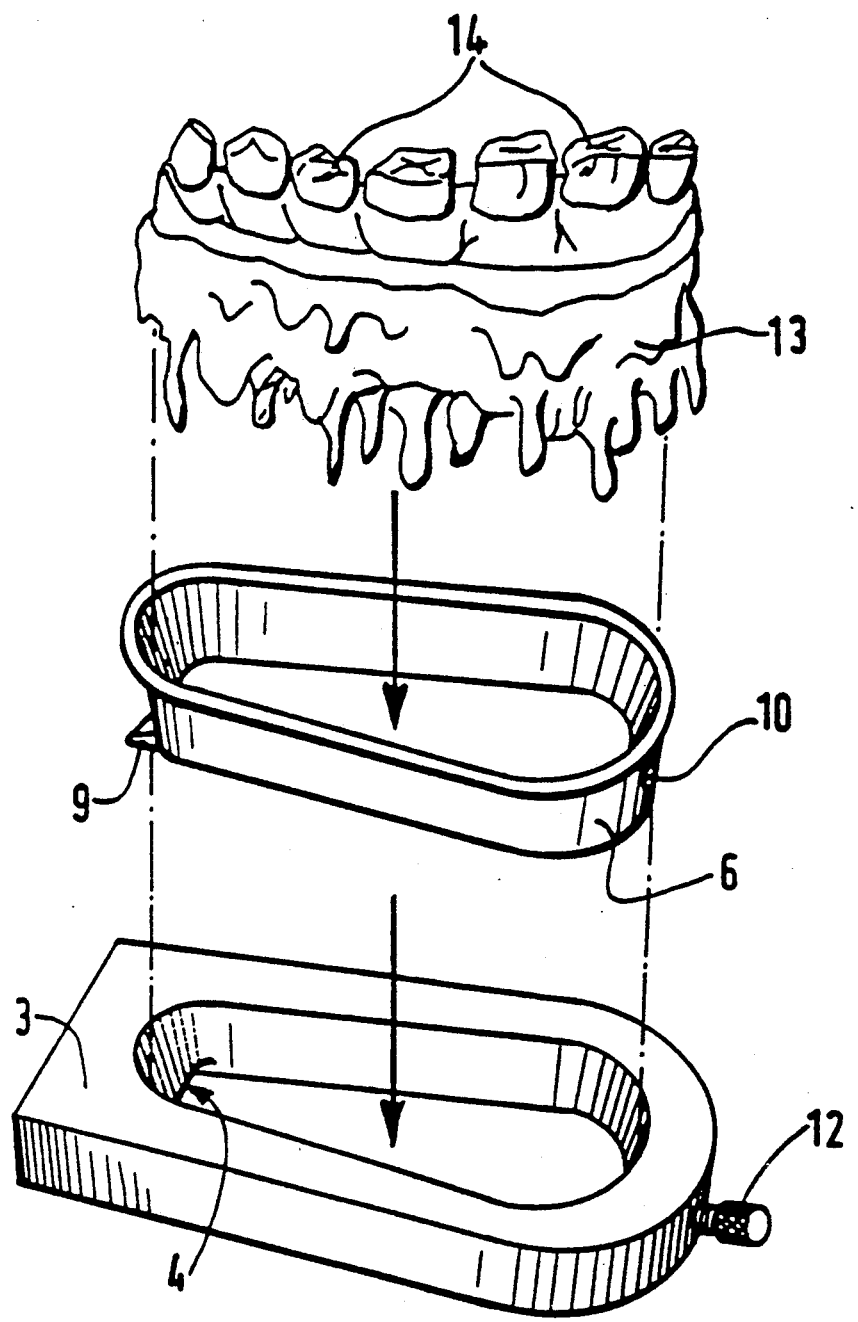
FIG. 6 shows a diagrammatic view of the stage of presentation of the first model element in the liquid plaster of the cupel/cup assembly.

The method for using the device according to the invention will be described with reference to FIG. 6.

First, the cupel (6) is introduced into the cup (3) taking care to first position the lug (9) in line with the notch (4) in the cup (3) (see FIG. 4), then the opposite lateral surface of the cupel (6) is lowered into the cup (3) until it engages perfectly in the cup (3). The cupel (6) is then held in the cup (3) by means of the screw (12) which is screwed as far as partial locking.

Once the cup/cupel assembly has been fixed in this way and placed on a plane surface, the cupel (6) is then filled with liquid plaster (13), in which the denture (14) of the model to be produced, constituting the first part thereof, is positioned by driving it in. After the plaster hardens, a complete lower or upper model is thus obtained, whose second part (15) is integral with the cupel (6).

In this way, after total solidification of the plaster, the assembly consisting respectively of the cupel (6), the denture (14) and said second part (15) constitutes the desired model, which can be used for producing the prosthesis.

Given that the cupel (6) is held in place and braced in the cup (3), said cupel is not affected by the expansion of the plaster during solidification of the latter. Indeed, the cupel (6) actually acts as a bridle on the expansion of the plaster, during its solidification. In this way, the assembly thus produced, consisting of the cupel and the model, can be reused many times until achieving the prosthesis which comes as close as possible to the occlusion conditions in the mouth of the patient to which it is intended to be adapted.

In this way the device according to the invention makes it possible first to overcome the problems associated with the expansion of the plaster, and also the fragility of the plaster models, given that said model is surrounded by the cupel (6). After the final use, the model can be removed from the cupel (6) by tearing the latter at the incipient break points situated, for example, on its main lateral surfaces.

Figure 8:
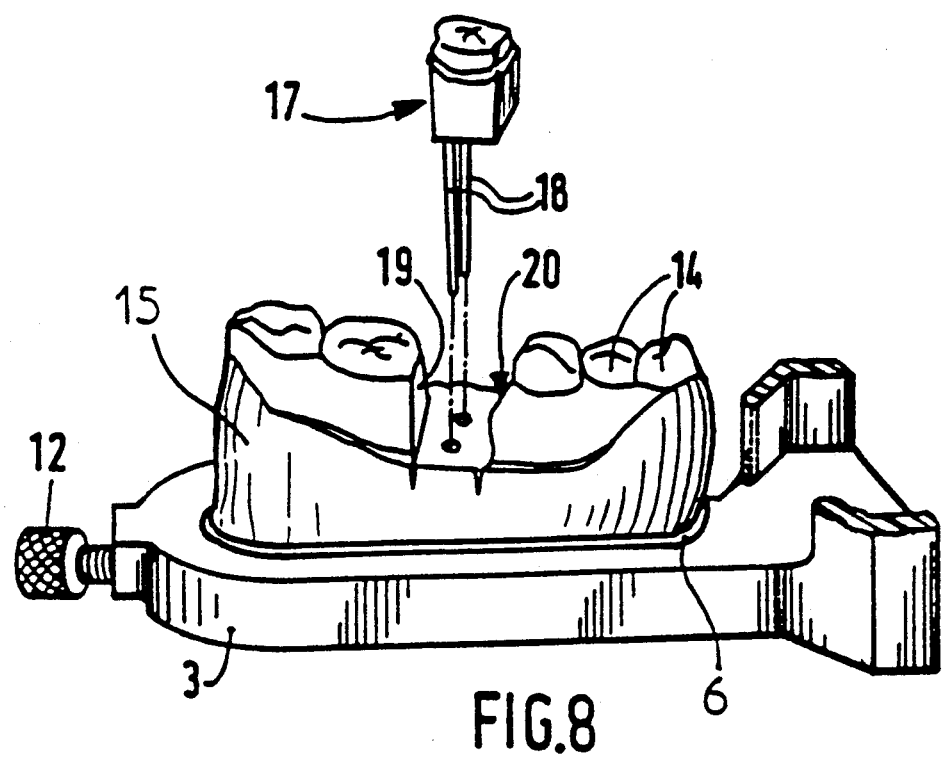
FIG. 8 shows a diagrammatic view of a model produced in accordance with the invention and having a removable zone called a "die".

As already mentioned, the cupel (6) does not have a base. In this way it is entirely possible to gain access to the rear surface (16) of a model and, thus, to the pin or needle serving as a support for a plaster +reconstitution assembly (17) forming a die, precisely in order to remove this assembly from the model, as has been moreover shown in FIG. 8. The die (17) thus formed is in fact easily produced by making two saw cuts in the transverse planes (19) and (20) of the model shown in FIG. 8. These transverse planes (19) and (20) define the surfaces of the die (17) which can then be removed or put back into position on the model, and this each time this proves necessary.

It should be stressed that the scope of the invention need not be limited to the example described hereinabove. The cupel (6) is generally designed to receive a model for a total or partial dental arch. Thus, its shape can be elongate, round, or adapted to the shape of an upper or lower dental arch. Similarly, it can be of a greater or lesser depth. Its internal lateral wall can be smooth or otherwise. As already mentioned, the base of the cupel can be open or closed. However, in all cases, it is intended to be adapted to the internal profile of the cup of the occlusion device or articulator receiving it, it being possible for the system for its anchorage in said cup to be of any adapted type.

I claim:

1. A device for the production of a plaster model, of total or partial dental arch replicas, used for dental reconstitutions, said device comprising:
    a cup member to be mounted on an occlusion device or articulator, said cup member having a recess formed therein defined by an inner wall of said cup;
    a cupel for receiving said plaster model, an outer peripheral wall of said cupel having a shape and size which substantially corresponds to said inner wall of said cup member; and
    means for securing said cupel in said cup;
    wherein said cupel is fixed in said cup when said plaster model is introduced therein, and thereafter said cupel is removable from said cup through operation of said securing means.

2. The device of claim 1, wherein said cup member has an elongate and closed peripheral contour, a first end of said cup member is fixed to said occlusion device or articulator, and said means for securing comprises a longitudinal screw arranged at a second end of said cup member, said longitudinal screw engaging said outer peripheral wall of said cupel when said cupel is arranged in said cup member.

3. The device of claim 2, wherein said outer peripheral wall of said cupel includes a recess formed therein for receiving an end of said longitudinal screw.

4. The device of claim 3, wherein said end of said longitudinal screw is in the form of a needle and said recess in said outer peripheral wall of said cupel is in the form of a conical recess aligned with the axis of the end of said screw and slightly of set relative to the generatrix of the cone of said recess when the cupel is arranged is said cup member, such that after the plaster model has been poured into said cupel, the cupel is slightly displaced toward a base of said cup member when the longitudinal screw is turned to secure said cupel in said cup member until the axis of the end of said longitudinal screw coincides with the generatrix of the cone of said recess.

5. The device of claim 2, wherein said means for securing said cupel includes an attachment lug formed on an end of said cupel opposite an end of said cupel which engages said longitudinal screw, said attachment lug engaging said cup member to secure said cupel in said cup member.

6. The device of claim 1, wherein said cupel has an open base and an outwardly extending peripheral shoulder which engages an upper surface of said cup member to limit the penetration of said cupel into said cup member.

7. The device of claim 10, wherein said cupel comprises high-impact polystyrene and said cup member comprises polyacetal.

8. A device for the production of a plaster model, of total or partial dental arch replicas, used for dental reconstitutions, said device comprising:
    a cup member to be mounted on an occlusion device or articulator, said cup member having a recess formed therein defined by an inner wall of said cup;
    a cupel for receiving said plaster model, wherein a wall of said cupel includes transverse orifices and incipient break points, and an outer periphery of said wall has a shape and size which substantially corresponds to said inner wall of said cup member;
    means for securing said cupel in said cup; and
    wherein said cupel is fixed in said cup when said plaster model is introduced therein, and thereafter said cupel is removable from said cup through operation of said securing means.

9. A method for producing a plaster model, of total or partial dental arch replicas, used for dental reconstitutions, said method comprising:
    providing a cup member to be mounted on an occlusion device or articulator, said cup member having a recess form therein defined by an inner wall of said cup;
    providing a cupel for receiving said plaster model, an outer peripheral wall of said cupel having a shape and size which substantially corresponds to said inner wall of said cup member;
    inserting and fixing said cupel in said cup member;
    filling said cupel with liquid plaster;
    positioning and driving into said liquid plaster a first part of said plaster model;
    hardening said plaster model; and
    removing said plaster model with said cupel fixed thereto from said cup member;
    wherein said cupel constitutes a base for said plaster model which can be laser positioned in a cup member associated with an occlusion device or articulator.

* * * * *